(12) United States Patent
Nakamura

(10) Patent No.: US 10,314,636 B2
(45) Date of Patent: Jun. 11, 2019

(54) TREATMENT APPARATUS AND METHOD FOR CONTROLLING THE SAME

(71) Applicant: OLYMPUS CORPORATION, Tokyo (JP)

(72) Inventor: Kotaro Nakamura, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 782 days.

(21) Appl. No.: 14/815,293

(22) Filed: Jul. 31, 2015

(65) Prior Publication Data

US 2015/0335375 A1  Nov. 26, 2015

Related U.S. Application Data

(63) Continuation of application No. PCT/JP2014/050827, filed on Jan. 17, 2014.

(30) Foreign Application Priority Data

Feb. 1, 2013  (JP) .................. 2013-018619

(51) Int. Cl.
*A61B 18/08* (2006.01)
*A61B 18/10* (2006.01)
(Continued)

(52) U.S. Cl.
CPC ............ *A61B 18/082* (2013.01); *A61B 18/10* (2013.01); *A61B 18/1445* (2013.01);
(Continued)

(58) Field of Classification Search
CPC ...... A61B 18/082; A61B 18/085; A61B 18/10; A61B 18/1445; A61B 2018/00619;
(Continued)

(56) References Cited

U.S. PATENT DOCUMENTS

2004/0092923 A1* 5/2004 Miura ................ A61B 18/085
606/28
2013/0245619 A1 9/2013 Yasunaga
(Continued)

FOREIGN PATENT DOCUMENTS

CN 103260538 A 8/2013
EP 2 653 125 A1 10/2013
(Continued)

OTHER PUBLICATIONS

Extended Supplementary European Search Report dated Sep. 9, 2016 in European Patent Application No. 14 74 6779.9.
(Continued)

*Primary Examiner* — Michael F Peffley
*Assistant Examiner* — Tigist S Demie
(74) *Attorney, Agent, or Firm* — Scully, Scott, Murphy & Presser, P.C.

(57) ABSTRACT

A treatment apparatus for treating a body tissue, the treatment apparatus having a drive circuit, an electric resistance pattern, a heat transfer plate, a temperature acquisition circuit, and a controller. The controller controlling the drive circuit to supply power to the electric resistance pattern based on a target temperature of the heat transfer plate and a temperature of the electric resistance pattern acquired by the temperature acquisition circuit.

6 Claims, 14 Drawing Sheets

(51) Int. Cl.
  *A61B 18/14* (2006.01)
  *A61B 18/00* (2006.01)
(52) U.S. Cl.
  CPC ... *A61B 18/085* (2013.01); *A61B 2018/00619* (2013.01); *A61B 2018/00642* (2013.01); *A61B 2018/00678* (2013.01); *A61B 2018/00702* (2013.01); *A61B 2018/00708* (2013.01); *A61B 2018/00714* (2013.01); *A61B 2018/00791* (2013.01)
(58) Field of Classification Search
  CPC .......... A61B 2018/00642; A61B 2018/00678; A61B 2018/00702; A61B 2018/00708; A61B 2018/00714; A61B 2018/00791
  See application file for complete search history.

(56) References Cited

U.S. PATENT DOCUMENTS

| | | |
|---|---|---|
| 2014/0074087 A1 | 3/2014 | Yasunaga |
| 2014/0142562 A1 | 5/2014 | Yasunaga |

FOREIGN PATENT DOCUMENTS

| | | |
|---|---|---|
| EP | 2 737 867 A1 | 6/2014 |
| JP | 2000-339039 A | 12/2000 |
| JP | 2001-190561 A | 7/2001 |
| JP | 2003-208964 A | 7/2003 |
| JP | 2005-110713 A | 4/2005 |
| JP | 2007-037845 A | 2/2007 |
| JP | 2009-247893 A | 10/2009 |
| JP | 2010-065661 A | 3/2010 |
| JP | 2012-125338 A | 7/2012 |
| JP | 2012-161566 A | 8/2012 |
| JP | 2013-022354 A | 2/2013 |
| WO | 2012/081514 A1 | 6/2012 |
| WO | 2012/161163 A1 | 11/2012 |

OTHER PUBLICATIONS

English translation of International Preliminary Report on Patentability dated Aug. 13, 2015 together with the Written Opinion, received in related International Application No. PCT/JP2014/050827.

International Search Report dated Aug. 14, 2012 together with the Written Opinion from related International Application No. PCT/JP2012/068610.

International Search Report dated Feb. 21, 2012 together with the Written Opinion from related International Application No. PCT/JP2011/078542.

International Search Report dated Apr. 15, 2014 together with the Written Opinion from related International Application No. PCT/JP2014/050827.

* cited by examiner

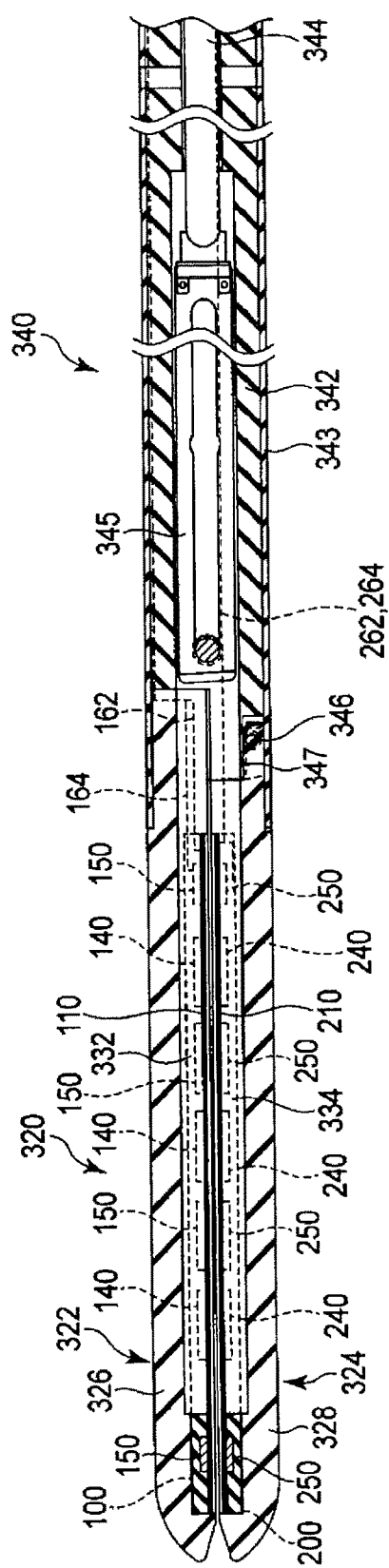

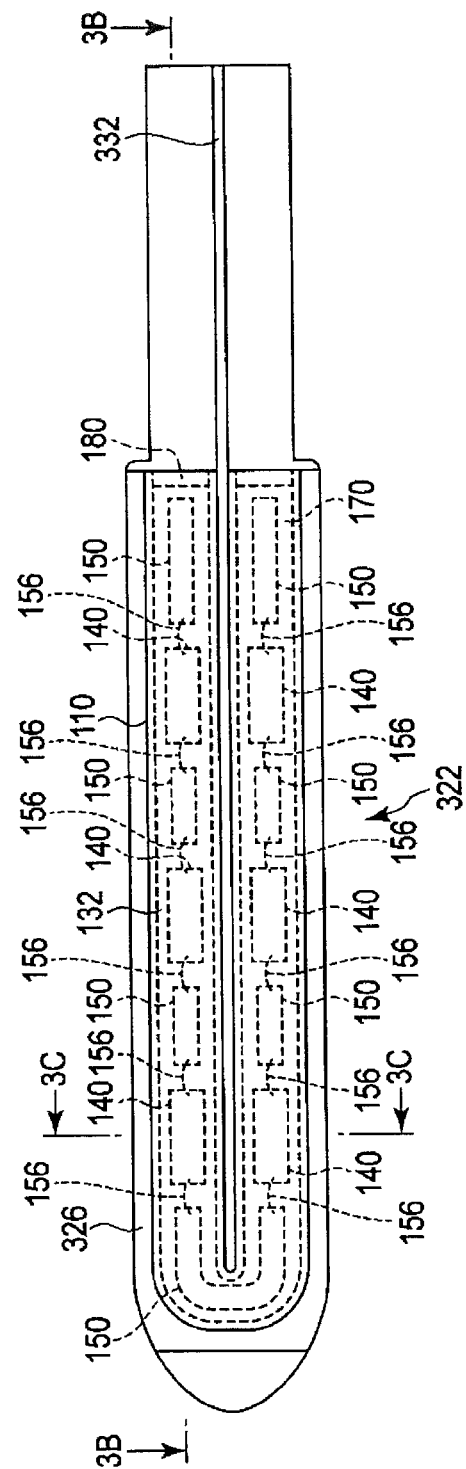

TREATMENT APPARATUS AND METHOD FOR CONTROLLING THE SAME

CROSS-REFERENCE TO RELATED APPLICATIONS

This application is a continuation of PCT International Application No. PCT/JP2014/050827, filed on Jan. 17, 2014, and claims priority to Japanese Patent Application No. JP 2013-018619, filed on Feb. 1, 2013. The entire contents of PCT International Application No. PCT/JP2014/050827 and Japanese Patent Application No. JP 2013-018619 are incorporated herein by this reference.

BACKGROUND

Technical Field

The present invention relates to a treatment apparatus and a method for controlling the same.

Background Art

There is generally known a treatment apparatus for treating body tissues by use of high frequency energy or thermal energy. For example, Japanese Patent Application Laid-Open No. 2012-125338 Publication and Japanese Patent Application Laid-Open No. 2012-161566 Publication disclose therein the following treatment apparatuses. That is, the treatment apparatuses include an openable/closable holding part for gripping a body tissue to be treated. A portion of the holding member contacting with a body tissue is provided with a high frequency electrode for applying a high frequency voltage. Further, the high frequency electrode is provided with a heat generation chip as an electrothermal conversion element for heating the high frequency electrode. The holding part is provided with a cutter. In use of such a treatment apparatus, the holding part first grips a body tissue. The holding part anastomoses the body tissue by applying a high frequency voltage to the body tissue and further heating the body tissue by use of the heat generation chip. Ends of the body tissue can be removed by the cutter provided in the holding part while they are joined.

For example, Japanese Patent Application Laid-Open No. 2012-125338 Publication discloses that in temperature control of the heat generation chip for heating a body tissue, a temperature of an electric resistance pattern is acquired based on a resistance value of the electric resistance pattern as a heat generator and a temperature of the high frequency electrode functioning as a heat transfer part contacting with the body tissue is estimated based on the temperature. Further, Japanese Patent Application Laid-Open No. 2012-125338 Publication discloses that power to be supplied to the heat generation chip is subjected to feedback control based on a difference between the estimated temperature of the high frequency electrode and a target temperature thereby to heat the body tissue at the target temperature.

Further, for example, Japanese Patent Application Laid-Open No. 2012-161566 Publication discloses that a temperature difference value between a temperature of the electric resistance pattern used for the above feedback control and a temperature of the high frequency electrode functioning as a heat transfer part is acquired based on the temperature of the electric resistance pattern when different magnitudes of power are supplied to the heat generation chip.

With the techniques according to Japanese Patent Application Laid-Open No. 2012-125338 Publication and Japanese Patent Application Laid-Open No. 2012-161566 Publication, in order to keep a temperature of the heat transfer part such as high frequency electrode at the target temperature, the target temperature of the electric resistance pattern is updated based on the temperature of the heat transfer part and the supplied power each time feedback is repeated. However, such control cannot accurately process the update of the target temperature of the electric resistance pattern and the update of the supplied power for achieving the target temperature at the same time depending on a performance of a used power supply or drive circuit, which can be unstable due to oscillation.

SUMMARY

It is an object of the present invention to provide a treatment apparatus capable of stable control and a method for controlling the same.

In one embodiment, a treatment apparatus for treating a body tissue is provided. The treatment apparatus comprises: a drive circuit configured to be controlled to supply power; an electric resistance pattern configured to generate heat based on the power supplied by the drive circuit; a heat transfer plate configured to contact the body tissue, wherein the heat transfer plate is arranged to be in thermal communication with the electric resistance pattern to transfer the heat generated by the electric resistance pattern to the body tissue; a temperature acquisition circuit configured to be controlled to acquire a temperature of the electric resistance pattern; and a controller configured to: in a first cycle, control the drive circuit to supply a first power to the electric resistance pattern; control the temperature acquisition circuit to acquire a first temperature of the electric resistance pattern; and control the drive circuit to stop supplying the first power when the first temperature of the electric resistance pattern reaches a target temperature of the heat transfer plate; in a subsequent cycle after the first cycle, control the temperature acquisition circuit to acquire a second temperature of the electric resistance pattern; calculate an offset value based on a difference between the target temperature of the heat transfer plate and the second temperature of the electric resistance pattern; calculate a subsequent target temperature based on the offset value; and calculate a second power to be supplied to the electric resistance pattern to heat the electric resistance pattern to the subsequent target temperature; and control the drive circuit to supply the second power to the electric resistance pattern.

In another embodiment, a method for controlling a treatment apparatus to treat a body tissue is provided. The treatment apparatus comprises: a drive circuit configured to be controlled to supply power; an electric resistance pattern configured to generate heat based on the power supplied by the drive circuit; a heat transfer plate configured to contact the body tissue, wherein the heat transfer plate is arranged to be in thermal communication with the electric resistance pattern to transfer the heat generated by the electric resistance pattern to the body tissue; and a temperature acquisition circuit configured to be controlled to acquire a temperature of the electric resistance pattern. The method comprises: in a first cycle, controlling the drive circuit to supply a first power to the electric resistance pattern; controlling the temperature acquisition circuit to acquire a first temperature of the electric resistance pattern; and controlling the drive circuit to stop supplying the first power when the first temperature of the electric resistance pattern reaches a target temperature of the heat transfer plate; and in a subsequent cycle after the first cycle, controlling the temperature acquisition circuit to acquire a second temperature of the electric resistance pattern; calculating an offset value based on a difference between the target temperature of the heat transfer plate and the second temperature of the electric resistance pattern; calculating a subsequent target temperature based on the offset value; calculating a second power to be supplied to the electric resistance pattern to heat the electric resistance pattern to the subsequent target temperature; and controlling the drive circuit to supply the second power to the electric resistance pattern.

BRIEF DESCRIPTION OF THE DRAWINGS

FIG. 2A is a schematic cross-section view illustrating an exemplary structure of a shaft and a holding part in an energy treatment tool according to each exemplary embodiment, which illustrates a state in which the holding part is closed;

FIG. 3A is a schematic plan view illustrating an exemplary structure of a first holding member in the holding part according to each exemplary embodiment;

DETAILED DESCRIPTION

First Exemplary Embodiment

Figure 1:
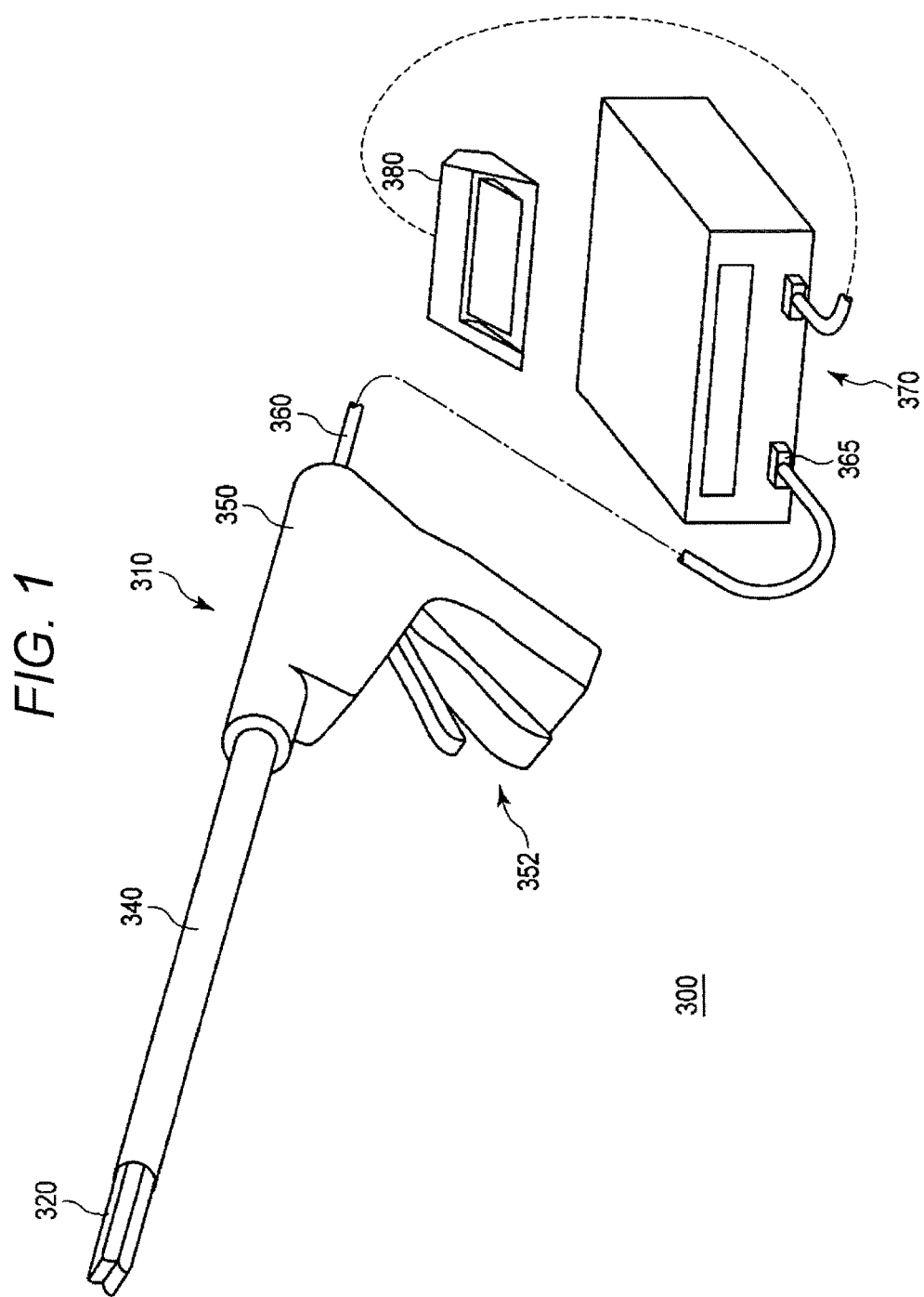
FIG. 1 is a schematic diagram illustrating an exemplary structure of a treatment system according to each exemplary embodiment.

A first exemplary embodiment according to the present invention will be described with reference to the drawings. A treatment apparatus according to the present exemplary embodiment is used to treat body tissues. The treatment apparatus operates high frequency energy and thermal energy on body tissues. As illustrated in FIG. 1, a treatment apparatus 300 comprises an energy treatment tool 310, a control device 370, and a foot switch 380.

The energy treatment tool 310 is a linear type surgical treatment tool penetrating through the abdominal wall for treatment, for example. The energy treatment tool 310 includes a handle 350, a shaft 340 attached on the handle 350, and a holding part 320 provided on the tip end of the shaft 340. The holding part 320 is a treatment part which is openable/closable and is directed to do treatments such as coagulation and incision of a body tissue by gripping the body tissue to be treated. For the following description, the side of the holding part 320 will be called tip end side and the side of the handle 350 will be called base end side. The handle 350 comprises a plurality of operation knobs 352 for operating the holding part 320. The handle 350 is further provided with a non-volatile memory (not illustrated) for storing therein eigenvalues and the like for the energy treatment tool 310. A shape of the energy treatment tool 310 illustrated herein is exemplary, and any other shape having the same function may be employed. For example, the shaft may be curved.

The handle 350 is connected to the control device 370 via a cable 360. Herein, the cable 360 and the control device 370 are connected with each other via a connector 365, and the connection is detachable. That is, the treatment apparatus 300 is configured to replace the energy treatment tool 310 per treatment. The control device 370 is connected with the foot switch 380. The foot-operated foot switch 380 may be replaced with a hand-operated switch or other switch. An operator operates the pedal of the foot switch 380 thereby to switch ON/OFF energy supply from the control device 370 to the energy treatment tool 310.

Figure 2B:
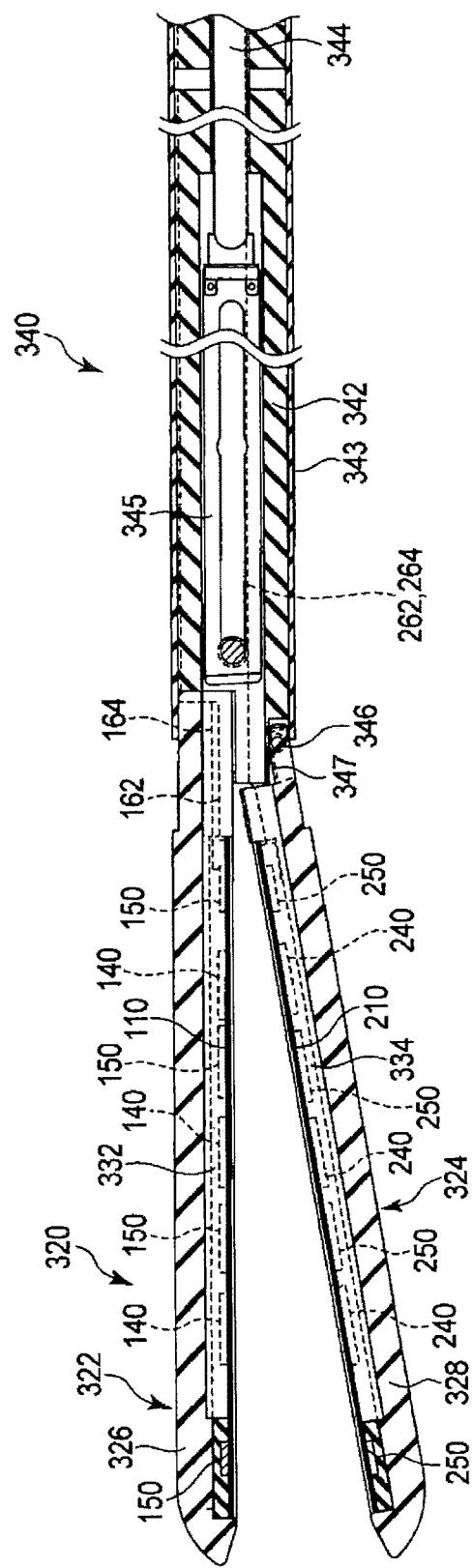
FIG. 2B is a schematic cross-section view illustrating an exemplary structure of the shaft and the holding part in the energy treatment tool according to each exemplary embodiment, which illustrates a state in which the holding part is opened.

An exemplary structure of the holding part 320 and the shaft 340 is illustrated in FIG. 2A and FIG. 2B. FIG. 2A illustrates a state in which the holding part 320 is closed and FIG. 2B illustrates a state in which the holding part 320 is opened. The shaft 340 comprises a tube 342 and a sheath 343. The tube 342 is fixed at its base end to the handle 350.

The sheath 343 is slidably arranged on the outer periphery of the tube 342 in the axial direction of the tube 342.

The holding part 320 is arranged on the tip end of the tube 342. The holding part 320 comprises a first holding member 322 and a second holding member 324. The base of the first holding member 322 is fixed on the tip end of the tube 342 in the shaft 340. On the other hand, the base of the second holding member 324 is rotatably supported on the tip end of the tube 342 in the shaft 340 by a support pin 346. Therefore, the second holding member 324 axially rotates about the support pin 346 and opens/closes relative to the first holding member 322.

In a state in which the holding part 320 is closed, a cross-section shape in which the base of the first holding member 322 and the base of the second holding member 324 are put together is circular. The second holding member 324 is energized by an elastic member 347 such as plate spring to open relative to the first holding member 322. When the sheath 343 is slid toward the tip end of the tube 342 so that the base of the first holding member 322 and the base of the second holding member 324 are covered by the sheath 343, as illustrated in FIG. 2A, the first holding member 322 and the second holding member 324 are closed against an energizing force of the elastic member 347. On the other hand, when the sheath 343 is slid toward the base end side of the tube 342, as illustrated in FIG. 2B, the second holding member 324 is opened relative to the first holding member 322 due to an energizing force of the elastic member 347.

The tube 342 is inserted with a first high frequency electrode current line 162 connected to a first high frequency electrode 110 and a second high frequency electrode current line 262 connected to a second high frequency electrode 210, which will be described later. The tube 342 is inserted with a pair of first heat generation chip current lines 164 connected to a heat generation chip 140 as heat generation member and a pair of second heat generation chip current lines 264 connected to a heat generation chip 240, which will be described later.

A drive rod 344 connected on its base end to one of the operation knobs 352 is movably arranged in the axial direction of the tube 342 inside the tube 342. A sheet-shaped cutter 345 forming a blade on its tip end is arranged on the tip end of the drive rod 344. When the operation knob 352 is operated, the cutter 345 is moved in the axial direction of the tube 342 via the drive rod 344. When the cutter 345 is moved toward the tip end, the cutter 345 is housed in a first cutter guide groove 332 and a second cutter guide groove 334 described later formed in the holding part 320.

Figure 3B:
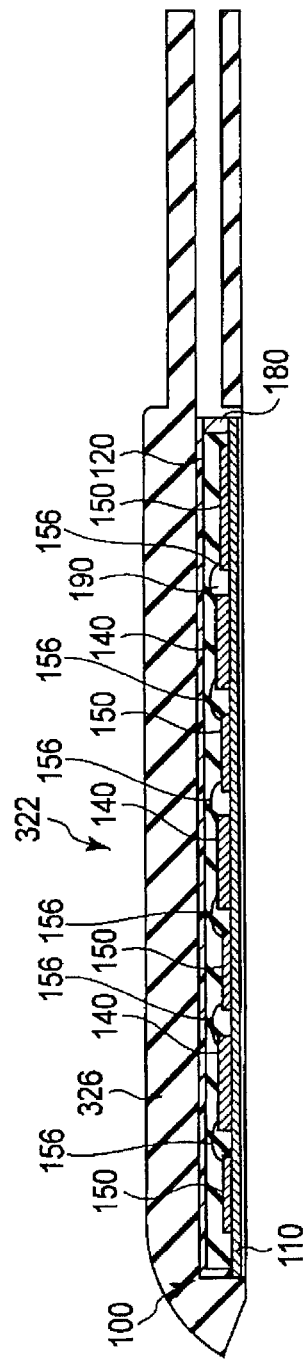
FIG. 3B is a schematic diagram illustrating an exemplary structure of the first holding member in the holding part according to each exemplary embodiment, which is a longitudinal cross-section view along the line 3B-3B illustrated in FIG. 3A.
Figure 3C:
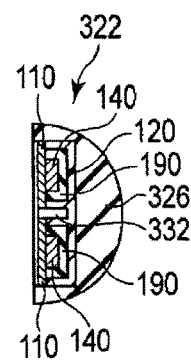
FIG. 3C is a schematic diagram illustrating an exemplary structure of the first holding member in the holding part according to each exemplary embodiment, which is a transverse cross-section view along the line 3C-3C illustrated in FIG. 3A.

The holding part 320 will be described with reference to FIG. 3A, FIG. 3B, and FIG. 3C. As illustrated in FIG. 3A, the first holding member 322 is formed with the first cutter guide groove 332 for guiding the cutter 345. The first holding member 322 is provided with the first high frequency electrode 110 formed of a copper thin plate, for example. The first high frequency electrode 110 is configured to contact with a body tissue on either main surface thereof (which will be called first main surface below). The first high frequency electrode 110 includes the first cutter guide groove 332, and thus its planar shape is U-shaped as illustrated in FIG. 3A. As illustrated in FIG. 2A and FIG. 2B, the first high frequency electrode current line 162 is electrically connected to a second main surface as the backside of the first main surface of the first high frequency electrode 110. The first high frequency electrode 110 is connected to the control device 370 via the first high frequency electrode current line 162 and the cable 360.

The heat generation chips 140 are arranged on the second main surface of the first high frequency electrode 110 which does not contact with a body tissue. Further, wiring members 150 for wiring to the heat generation chips 140 are arranged on the second main surface. A first cover member 120 is arranged to cover the heat generation chips 140, the wirings including the wiring members 150, and the first high frequency electrode 110. The first cover member 120 is made of resin, for example. An end sealing agent 180 is filled in the base end of the first high frequency electrode 110 and the first cover member 120. A space surrounded by the first high frequency electrode 110, the first cover member 120 and the end sealing agent 180 is inserted with an insulative sealing agent 190. The first cover member 120, the end sealing agent 180 and the sealing agent 190 are omitted in their illustration from FIG. 2A and FIG. 2B for simplified illustration. A first electrode part 100 surrounded by the first high frequency electrode part 110 and the first cover member 120 is formed in this way. The first electrode part 100 is embedded in and fixed on a first holding member main body 326 with an electric insulation property and a thermal insulation property.

As illustrated in FIG. 2A and FIG. 2B, the second holding member 324 is symmetrical in its shape to the first holding member 322, and has the same structure as the first holding member 322. That is, the second holding member 324 is formed with the second cutter guide groove 334 opposite to the first cutter guide groove 332. Further, the second holding member 324 is provided with the second high frequency electrode 210 opposite to the first high frequency electrode 110. The second high frequency electrode 210 is configured to contact with a body tissue on either main surface thereof. The second high frequency electrode 210 is connected to the control device 370 via the second high frequency electrode current line 262 and the cable 360.

The heat generation chips 240 similar to the heat generation chips 140 are joined on a surface of the second high frequency electrode 210 which does not contact with a body tissue. A second cover member similar to the first cover member 120 is arranged to cover the heat generation chips 240, the wirings including wiring members 250 for connecting to the heat generation chips 240, and the second high frequency electrode 210. An end sealing agent is filled in the base end of the second high frequency electrode 210 and the second cover member. An insulative sealing agent is filled in a space surrounded by the second high frequency electrode 210, the second cover member, and the end sealing agent. A second electrode part 200 surrounded by the second high frequency electrode 210 and the second cover member 220 is formed in this way. The second electrode part 200 is embedded in and fixed on a second holding member main body 328.

Figure 4A:
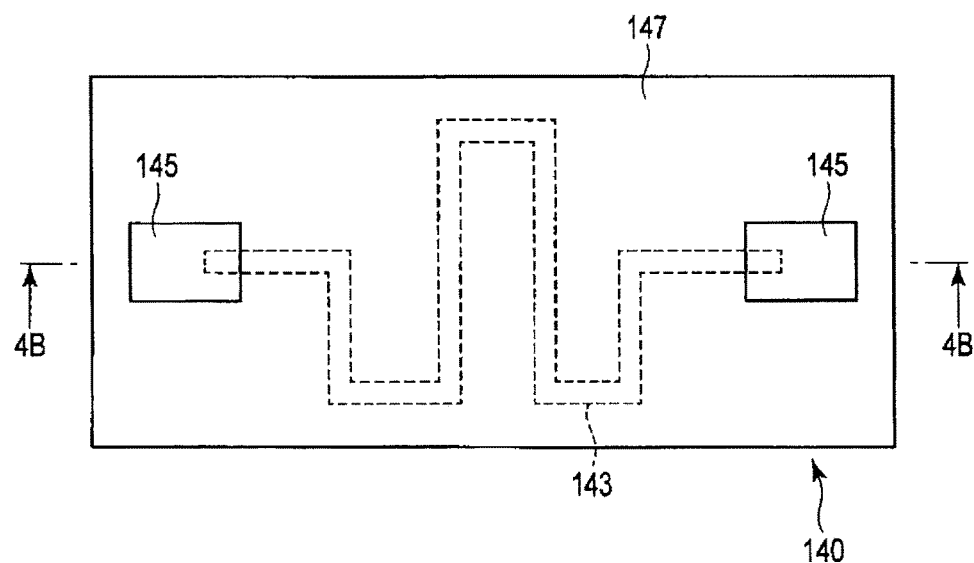
FIG. 4A is a schematic top view illustrating an exemplary structure of a heat generation chip according to each exemplary embodiment.
Figure 4B:
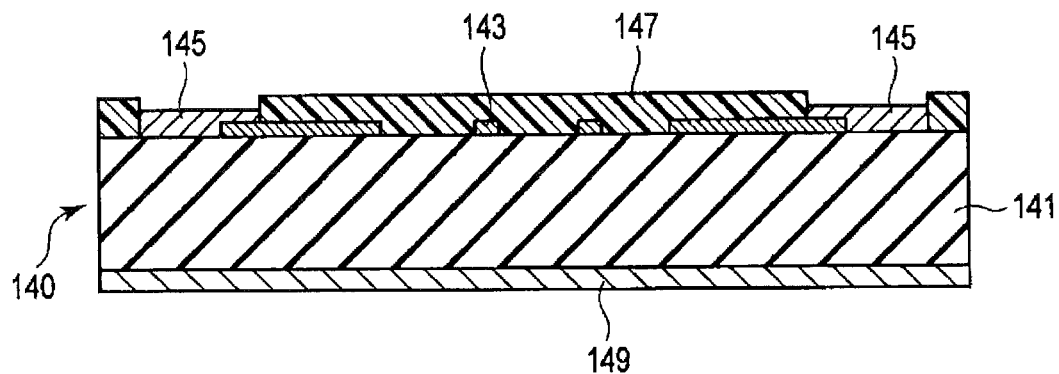
FIG. 4B is a schematic diagram illustrating an exemplary structure of the heat generation chip according to each exemplary embodiment, which is a cross-section view along the line 4B-4B illustrated in FIG. 4A.

The first electrode part 100 will be described in detail. The second electrode part 200 has the same structure as the first electrode part 100, and thus the description of the second electrode part 200 will be omitted. The heat generation chip 140 will be described with reference to FIG. 4A and FIG. 4B. Herein, FIG. 4A is a top view and FIG. 4B is a cross-section view along the line 4B-4B illustrated in FIG. 4A. The heat generation chip 140 is formed of a substrate 141 made of a highly heat-conductive material such as alumina nitride or alumina. A resistance pattern 143 such as Pt thin film for heat generation is formed on either main surface of the substrate 141. Electrodes 145, each of which can be formed to be rectangular in shape, are arranged near the two short sides of the rectangular surface of the substrate 141. Herein, the electrodes 145 are connected to the ends of the resistance pattern 143. An insulative film 147 made of polyimide, for example, is formed on the surface of the substrate 141 including the top of the resistance pattern 143 except the parts where the electrodes 145 are formed.

A joint metal layer 149 is formed on the entire backside of the substrate 141. The electrodes 145 and the joint metal layer 149 can each be a multilayer film made of Ti, Cu, Ni and Au, for example. The electrodes 145 and the joint metal layer 149 have a stable intensity against soldering or the like. The joint metal layer 149 is provided for stable joint when the heat generation chip 140 is soldered on the first high frequency electrode 110.

The heat generation chips 140 are arranged on a surface (second main surface) as the backside of a surface (first main surface) of the first high frequency electrode 110 which contacts with a body tissue. Herein, the heat generation chip 140 is fixed by soldering the surface of the joint metal layer 149 and the second main surface of the first high frequency electrode 110. Conductive paste may be used for the fixing. The heat generation chips 240 fixed on the second high frequency electrode 210 also have the same structure as the heat generation chips 140.

Figure 5:
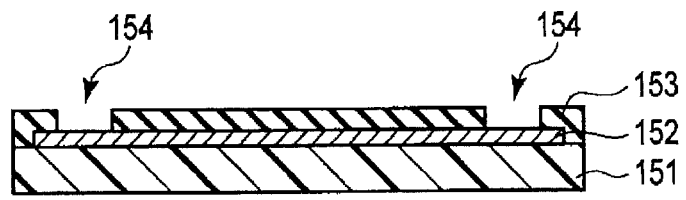
FIG. 5 is a schematic cross-section view illustrating an exemplary structure of a wiring member according to each exemplary embodiment.

The wiring member 150 is a flexible print board, for example. A schematic cross-section view of the wiring member 150 is illustrated in FIG. 5. As illustrated, a substrate 151 made of, for example, polyimide is formed with a wiring pattern 152 made of, for example, copper. The wiring pattern 152 is covered with an insulative film 153. Parts of the wiring pattern 152 are not covered with the insulative film 153 and the exposed wiring patterns 152 function as electrodes 154. The wiring member 150 is different in its size or shape as needed, but a basic structure thereof is as described above. The wiring member 150 may employ a foil-shaped or plate-shaped wiring member such as glass epoxy board instead of the flexible board.

Figure 6:
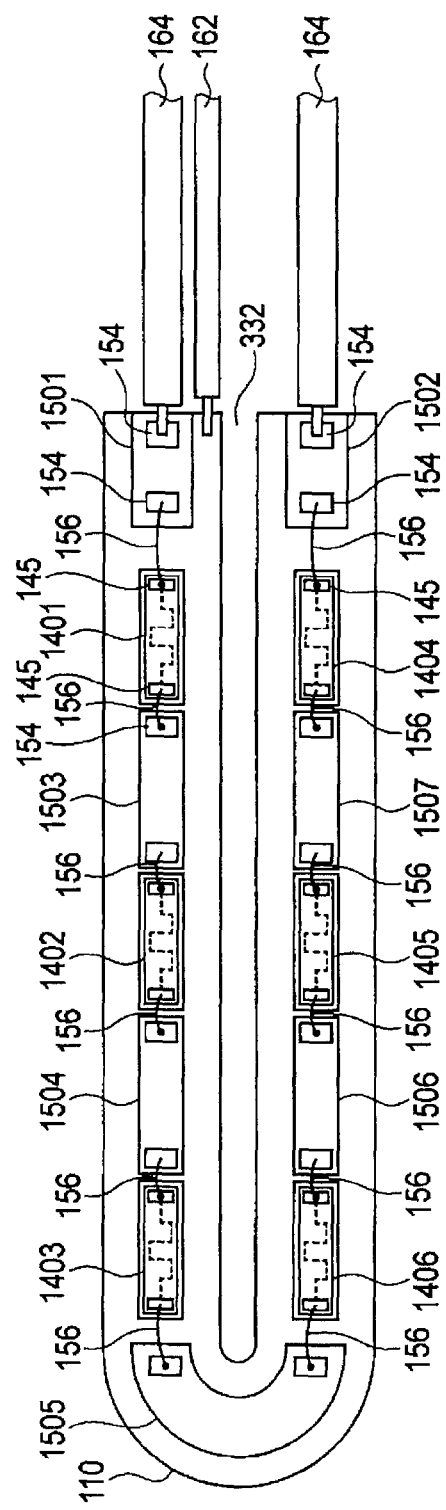
FIG. 6 is a schematic plan view illustrating an exemplary structure of a first high frequency electrode, heat generation chips, wiring members, and various wirings according to each exemplary embodiment.

The first high frequency electrode 110, the heat generation chips 140 on the first high frequency electrode 110, and the electric connections therebetween will be described with reference to FIG. 6. As illustrated in FIG. 6, the first high frequency electrode 110 has a U-shaped plane to form the first cutter guide groove 332.

Six heat generation chips 140 (1401-1406) are discretely arranged on the first high frequency electrode 110. That is, the heat generation chips 140 are arranged three by three in two lines symmetrically across the first cutter guide groove 332 from the base end toward the tip end. The heat generation chips 140 arranged in one line will be called first heat generation chip 1401, second heat generation chip 1402, and third heat generation chip 1403 in order from the base end, respectively. Similarly, the heat generation chips arranged in the other line will be called fourth heat generation chip 1404, fifth heat generation chip 1405, and sixth heat generation chip 1406 in order from the base end, respectively.

The wiring members 150 (1501-1507) are arranged on the first high frequency electrode 110 for connecting the heat generation chips 140. The wiring members 150 are fixed by use of adhesive resin, for example. At first, a wiring member 150 is arranged at the base end on the side where the first heat generation chip 1401 is arranged. The wiring member 150 will be called first wiring member 1501. Similarly, a second wiring member 1502 is arranged at the base end of the first high frequency electrode 110 on the side where the fourth heat generation chip 1404 is arranged.

One of a pair of first heat generation chip current lines 164 is electrically connected to the electrode 154 on the base end of the first wiring member 1501. Similarly, the other of the pair of first heat generation chip current lines 164 is electrically connected to the electrode 154 on the base end of the second wiring member 1502. The first high frequency electrode current line 162 is electrically connected to the base end of the first high frequency electrode 110.

The electrode 154 on the tip end of the first wiring member 1501 is electrically connected with the electrode 145 on the base end of the first heat generation chip 1401 via a wire 156 by wire bonding. In this way, the first heat generation chip current line 164 is electrically connected to the first heat generation chip 1401 via the first wiring member 1501. Similarly, the first heat generation chip current line 164 is electrically connected to the fourth heat generation chip 1404 via the second wiring member 1502.

A third wiring member 1503 is arranged between the first heat generation chip 1401 and the second heat generation chip 1402 on the first high frequency electrode 110. The electrode 154 on the base end of the third wiring member 1503 is electrically connected with the electrode 145 on the tip end of the first heat generation chip 1401 via the wire 156 by wire bonding. Similarly, the electrode 154 on the tip end of the third wiring member 1503 is electrically connected to the electrode 145 on the base end of the second heat generation chip 1402 via the wire 156 by wire bonding. In this way, the first heat generation chip 1401 and the second heat generation chip 1402 are electrically connected with each other in series.

Similarly, a fourth wiring member 1504 is arranged between the second heat generation chip 1402 and the third heat generation chip 1403. The second heat generation chip 1402 and the third heat generation chip 1403 are electrically connected with each other in series via the fourth wiring member 1504. A fifth wiring member 1505 is arranged between the third heat generation chip 1403 and the sixth heat generation chip 1406. The third heat generation chip 1403 and the sixth heat generation chip 1406 are electrically connected with each other in series via the fifth wiring member 1505. Similarly, the sixth heat generation chip 1406 and the fifth heat generation chip 1405 are electrically connected with each other in series via a sixth wiring member 1506. The fifth heat generation chip 1405 and the fourth heat generation chip 1404 are electrically connected with each other in series via a seventh wiring member 1507. As described above, the six heat generation chips 140 are connected in series between the pair of first heat generation chip current lines 164.

Each heat generation chip 140 is connected to the control device 370 via the first heat generation chip current lines 164 and the cable 360. The control device 370 controls power to be supplied to the heat generation chip 140. A current output from the control device 370 flows in each resistance pattern 143 of each heat generation chip 140. Consequently, each resistance pattern 143 generates heat. When the resistance pattern 143 generates heat, the heat is transferred to the first high frequency electrode 110. A body tissues contacting with the first high frequency electrode 110 is cauterized by the heat.

Figure 7:
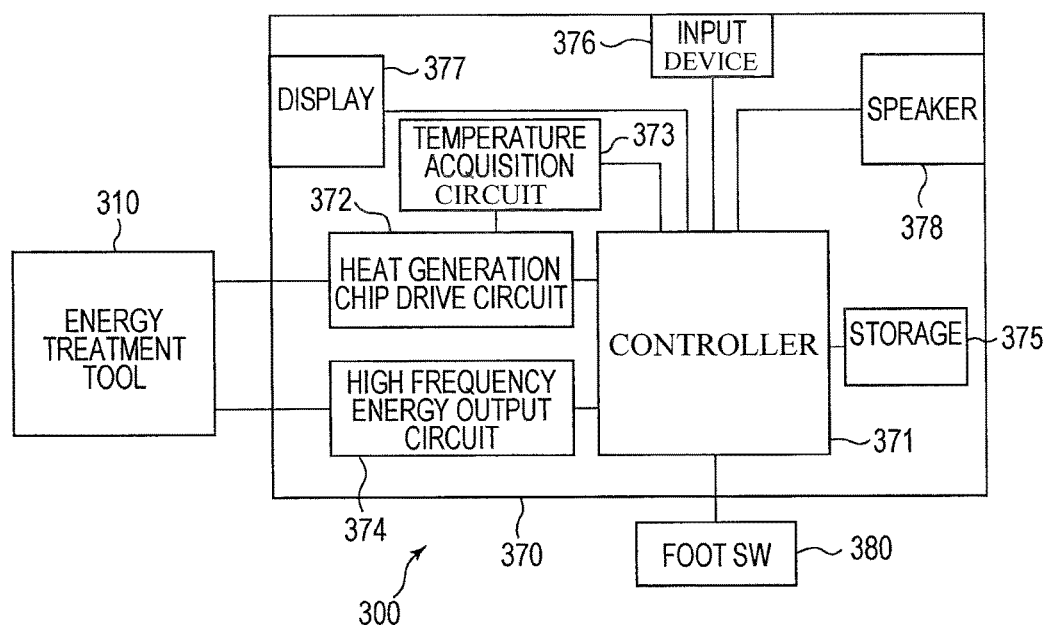
FIG. 7 is a block diagram illustrating an exemplary structure of a control device according to each exemplary embodiment.

The control device 370 will be described. As illustrated in FIG. 7, the control device 370 comprises a controller 371, a heat generation chip drive circuit 372, a temperature acquisition circuit 373, a high frequency energy output circuit 374, a storage 375, an input device 376, a display 377, and a speaker 378. The controller 371 is connected to each part in the control device 370, and controls each part in the control device 370. The high frequency energy output circuit 374 is connected to the energy treatment tool 310, and drives the first high frequency electrode 110 and the second high frequency electrode 210 in the energy treatment tool 310 under control of the controller 371. That is, the high frequency energy output circuit 374 applies a high frequency voltage to the first high frequency electrode 110 and the second high frequency electrode 210 via the first high frequency electrode current line 162 and the second high frequency electrode current line 262.

The heat generation chip drive circuit 372 is connected to the energy treatment tool 310, and drives each heat generation chip 140 and each heat generation chip 240 in the energy treatment tool 310 under control of the controller 371. That is, the heat generation chip drive circuit 372 supplies power to each resistance pattern 143 of the heat generation chips 140 and the heat generation chips 240 for heating via the first heat generation chip current lines 164 and the second heat generation chip current lines 264 under control of the controller 371.

The temperature acquisition circuit 373 has a function of acquiring a resistance value of each resistance pattern 143 of the heat generation chip 140 and the heat generation chip 240 based on a voltage applied to the heat generation chip 140 and the heat generation chip 240 and a current flowing therein at this time. The resistance value of the resistance pattern 143 changes depending on a temperature of the resistance pattern 143. The storage 375 stores therein a relationship between previously-acquired temperature and resistance value of the resistance pattern 143. The temperature acquisition circuit 373 acquires a temperature of the resistance pattern 143 by use of a relationship between temperature and resistance value of the resistance pattern 143 based on the resistance value of the resistance pattern 143. The temperature acquisition circuit 373 outputs the acquired temperature of the resistance pattern 143, or the temperatures of the heat generation chip 140 and the heat generation chip 240 to the controller 371. Since the temperature is acquired based on the resistance value of the resistance pattern 143, a temperature sensor does not need to be additionally provided, which is advantageous in downsizing the first electrode part 100 and the second electrode part 200.

The controller 371 stores the temperatures of the heat generation chip 140 and the heat generation chips 240 acquired from the temperature acquisition circuit 373 in the storage 375, and reads them as needed. The controller 371 calculates power to be supplied to the heat generation chip 140 and the heat generation chip 240 by use of the temperatures of the heat generation chip 140 and the heat generation chip 240. The controller 371 controls the heat generation chip drive circuit 372 thereby to supply the heat generation chip 140 and the heat generation chip 240 with the calculated power.

The controller 371 is connected with the foot switch (SW) 380, and is powered ON for treatment by the energy treatment tool 310 and is powered OFF for stopping a treatment from the foot switch 380. The input device 376 inputs various settings of the controller 371. The display 377 displays various settings of the controller 371. The storage 375 stores therein various items of data required for the operations of the control device 370. The speaker 378 outputs an alarm sound or the like.

The operations of the treatment apparatus 300 according to the present exemplary embodiment will be described below. The operator previously operates the input device 376 in the control device 370 to set the output conditions of the treatment apparatus 300, such as setting power for high frequency energy output, target temperature for thermal energy output, and heating time. The treatment apparatus 300 may be configured such that the respective values are independently set or a set of setting values is selected depending on an operation. In the present exemplary embodiment, a target temperature of the first high frequency electrode 110 and the second high frequency electrode 210 due to thermal energy output is assumed as a target temperature T_target.

The holding part 320 and the shaft 340 in the energy treatment tool 310 are inserted into the abdominal cavity via the peritoneum, for example. The operator operates the operation knobs 352 to open/close the holding part 320 so that a body tissue to be treated is gripped by the first holding member 322 and the second holding member 324. At this time, the body tissue to be treated contacts on the first main surface of the first high frequency electrode 110 provided on the first holding member 322 and the first main surface of the second high frequency electrode 210 provided on the second holding member 324.

When the body tissue to be treated is gripped by the holding part 320, the operator operates the foot switch 380. When the foot switch 380 is turned ON, high frequency power for preset power is supplied from the control device 370 to the first high frequency electrode 110 and the second high frequency electrode 210 via the first high frequency electrode current line 162 passing inside the cable 360. The supplied power is on the order of 20 W to 80 W, for example. Consequently, the body tissue generates heat and the tissue is cauterized. The tissue modifies and coagulates due to the cauterization.

After the control device 370 stops outputting high frequency energy, each of the heat generation chip 140 and the heat generation chip 240 is supplied with power such that the temperatures of the first high frequency electrode 110 and the second high frequency electrode 210 reach the target temperature. Herein, the target temperature is 200° C., for example. At this time, a current flows though the resistance pattern 143 of each heat generation chip 140 from the control device 370 via the cable 360 and the first heat generation chip current lines 164. The resistance pattern 143 of each heat generation chip 140 generates heat by the current. The heat generated by the resistance pattern 143 is transferred to the first high frequency electrode 110 via the substrate 141 and the joint metal layer 149. Consequently, the temperature of the first high frequency electrode 110 increases. Similarly, the heat generation chip 240 is supplied with power from the control device 370 via the cable 360 and the second heat generation chip current lines 264, and the heat generation chip 240 generates heat. The temperature of the second high frequency electrode 210 increases due to the heat generated by the heat generation chip 240.

The body tissue contacting with the first high frequency electrode 110 or the second high frequency electrode 210 is further cauterized and further coagulated by the heat. When the body tissue coagulates by the heating, the thermal energy stops being output. The operator finally operates the operation knobs 352 to move the cutter 345, thereby cutting the body tissue. The treatment of the body tissue is completed with the above operations.

The heating treatment by use of the heat generation chip 140 and the first high frequency electrode 110 as well as the heat generation chip 240 and the second high frequency electrode 210 will be described in more detail. The temperature control of the first electrode part 100 and the second electrode part 200 by the controller 371 will be described with reference to the flowchart illustrated in FIG. 8. The first electrode part 100 and the second electrode part 200 have the same structure, and thus the first electrode part 100 will be described below by way of example. The second electrode part 200 may be separately controlled similarly to the first electrode part 100. Further, with reference to power to be supplied to the heat generation chips 140 in the first electrode part, there may be controlled such that as much power as the power to be supplied to the heat generation chips 140 in the first electrode part is supplied to the heat generation chips 240 in the second electrode part 200.

In step S101, the controller 371 starts counting a first elapsed time t_c1 indicating an elapsed time after the heat generation chip 140 starts heating the first high frequency electrode 110. In step S102, the controller 371 causes the heat generation chip drive circuit 372 to supply the heat generation chip 140 with maximum power Pmax. In step S103, the controller 371 causes the temperature acquisition circuit 373 to acquire a temperature T_heat of the heat generation chip 140. At this time, the temperature acquisition circuit 373 acquires a resistance value of the resistance pattern 143 of the heat generation chip 140 based on a voltage applied to the heat generation chip 140 and a current flowing therein. The temperature acquisition circuit 373 calculates a temperature of the resistance pattern 143 based on the resistance value, and a relationship between resistance value and temperature. The calculated temperature of the resistance pattern 143 is assumed as the temperature T_heat of the heat generation chip 140. The controller 371 acquires the temperature T_heat of the heat generation chip 140 from the temperature acquisition circuit 373. Subsequently, the controller 371 determines whether the temperature T_heat of the heat generation chip 140 is higher than the target temperature T_target. When it is determined that the temperature T_heat of the heat generation chip 140 is not higher than the target temperature T_target, the processing returns to step S102 and the processing in step S102 is repeated. On the other hand, when it is determined that the temperature T_heat of the heat generation chip 140 is higher than the target temperature T_target, the processing proceeds to step S104.

In step S104, the controller 371 acquires a period t_i which is an elapsed time after the heat generation chip 140 is supplied with power and until the temperature T_heat of the heat generation chip 140 reaches the target temperature T_target. The period t_i is used as a sampling cycle for acquiring an inspection temperature T_ins as described later.

In step S105, the controller 371 causes the heat generation chip drive circuit 372 to stop supplying the heat generation chip 140 with power. In step S106, the controller 371 causes the heat generation chip drive circuit 372 to supply the heat generation chip 140 with predetermined inspection power P_ins. Herein, the inspection power P_ins is much lower than the power for heating the first high frequency electrode 110. Therefore, the temperature of the resistance pattern 143 of the heat generation chip 140 is equal to the temperature of the first high frequency electrode 110, or the temperature of a body tissue being heated.

In step S107, the controller 371 causes the temperature acquisition circuit 373 to calculate the inspection temperature T_ins which is a temperature of the heat generation chip 140 when the inspection power P_ins is supplied based on the resistance value of the resistance pattern 143 of the heat generation chip 140 when the inspection power P_ins is supplied. The controller 371 acquires the inspection temperature T_ins from the temperature acquisition circuit 373. The inspection temperature T_ins is calculated after a predetermined time elapses since the power supplied to the heat generation chip 140 is switched to the inspection power P_ins and the temperature of the resistance pattern 143 of the heat generation chip 140 is equal to the temperature of the first high frequency electrode 110 to be stabilized. The inspection temperature T_ins is acquired as in the present exemplary embodiment so that the temperature of the first high frequency electrode 110 may be found based on the resistance value of the resistance pattern 143.

In step S108, the controller 371 calculates a subsequent target temperature Tn_target of the heat generation chips 140 in Equation (1).

$$Tn\_target = T\_target + (T\_target - T\_ins) \quad (1)$$

That is, a difference between the target temperature T_target and the inspection temperature T_ins is assumed as an offset value for correcting the difference, and the offset value is added to the target temperature T_target. In step S109, the controller 371 resets a second elapsed time t_c2 indicating an elapsed time after the target temperature is reset, and starts counting it.

In step S110, the controller 371 performs a target temperature control operation. In the target temperature control operation, the controller 371 causes the temperature acquisition circuit 373 to calculate the temperature T_heat of the heat generation chip 140 at a predetermined sampling cycle, and acquires the temperature T_heat of the heat generation chip 140. The controller 371 performs feedback control based on the temperature T_heat of the heat generation chip 140 such that the heat generation chip 140 reaches the subsequent target temperature Tn_target. The feedback control employs a control method such as PD control or PID control. In the target temperature control operation, the controller 371 determines power to be supplied to the heat generation chip 140, and causes the heat generation chip drive circuit 372 to supply the heat generation chip 140 with power. Consequently, the first high frequency electrode 110 is heated and a body tissue contacting with the first high frequency electrode 110 is heated.

In step S111, the controller 371 determines whether the first elapsed time t_c1 is shorter than a preset heating time. When the elapsed time is shorter than the heating time, the processing proceeds to step S112. In step S112, the controller 371 determines whether the second elapsed time t_c2 is shorter than the period t_i. When it is determine that the second elapsed time t_c2 is shorter than the period t_i, the processing returns to step S110 to continue the target temperature control operation. On the other hand, when it is determined that the second elapsed time t_c2 is not shorter than the period t_i in step S112, the processing returns to step S105. The feedback control cycle which is also the loop processing cycle from step S110 to step S112 or the sampling cycle for causing the temperature acquisition circuit 373 to calculate the temperature T_heat of the heat generation chip 140 is 0.1 second, for example. The period t_i is longer than 0.1 second, for example.

In the determination in step S111, when it is determined that the first elapsed time t_c1 is not shorter than the preset heating time, the processing proceeds to step S113. That is, when the elapsed time after the start of power supply exceeds the heating time, the processing proceeds to step S113. In step S113, the controller 371 stops supplying the heat generation chip 140 with power, and terminates the processing.

Figure 9:
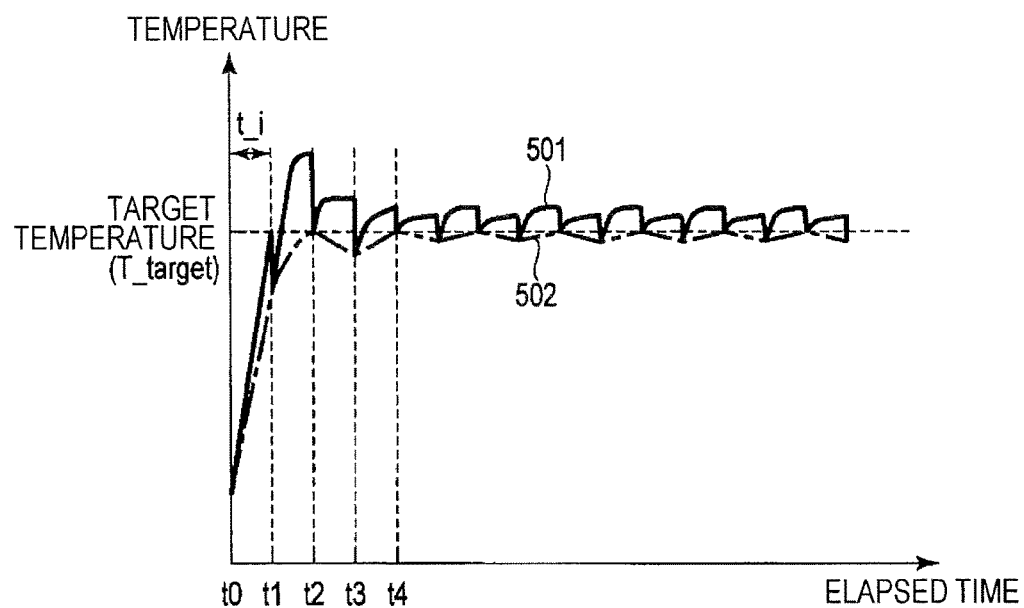
FIG. 9 is a diagram illustrating an exemplary relationship between an elapsed time, and the heat generation chip as well as the first high frequency electrode according to the first exemplary embodiment.
Figure 10:
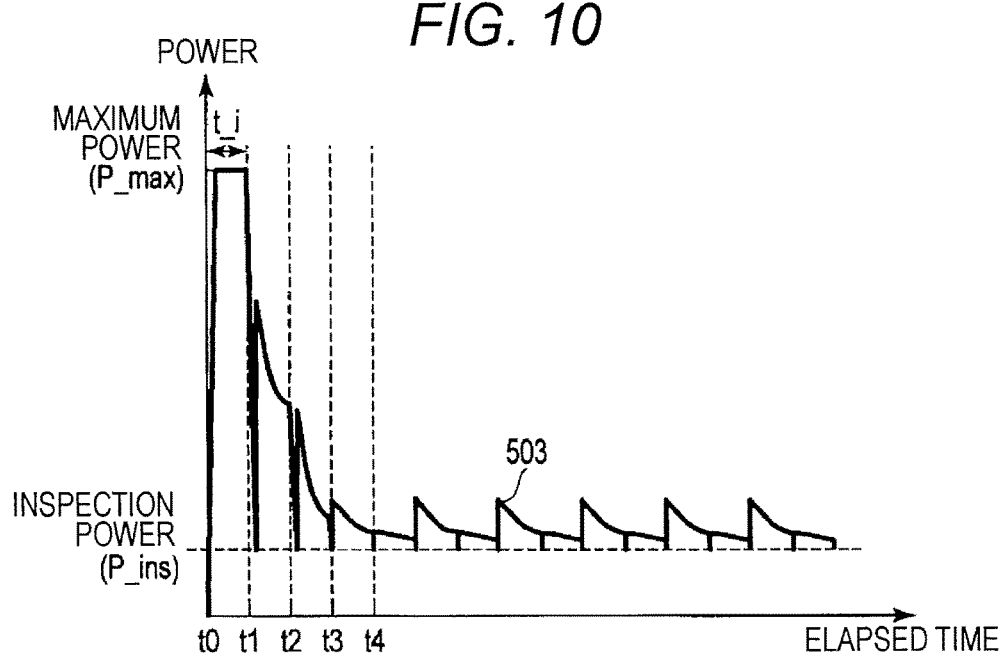
FIG. 10 is a diagram illustrating an exemplary relationship between an elapsed time and power supplied to the heat generation chip according to the first exemplary embodiment.

A change in temperature of the heat generation chip 140 and a change in temperature of the first high frequency electrode 110 relative to an elapsed time during the above processings are illustrated in FIG. 9. In FIG. 9, solid line 501 indicates a change in temperature T_heat of the heat generation chip 140, and dashed-dotted line 502 indicates a change in temperature T_hfe of the first high frequency electrode 110. A change in power supplied to the heat generation chip 140 relative to an elapsed time in FIG. 9 is illustrated in FIG. 10. In FIG. 10, solid line 503 indicates power supplied to the heat generation chip 140. An elapsed time t0 indicates the start of heating.

Figure 11:
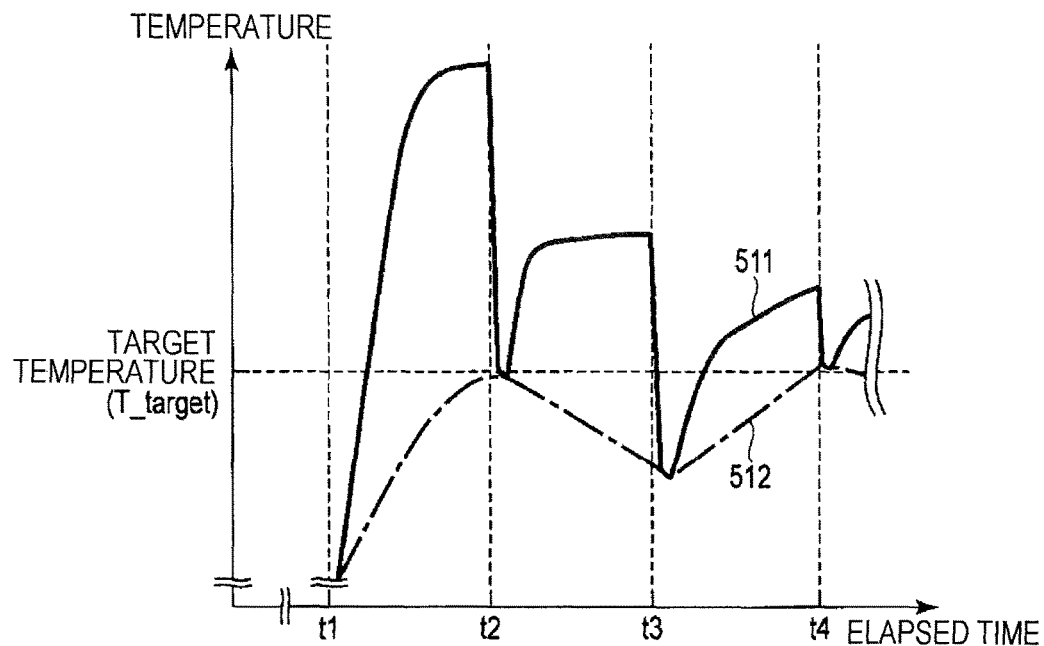
FIG. 11 is an enlarged diagram illustrating an exemplary relationship between an elapsed time, and the heat generation chip as well as the first high frequency electrode according to the first exemplary embodiment.
Figure 12:
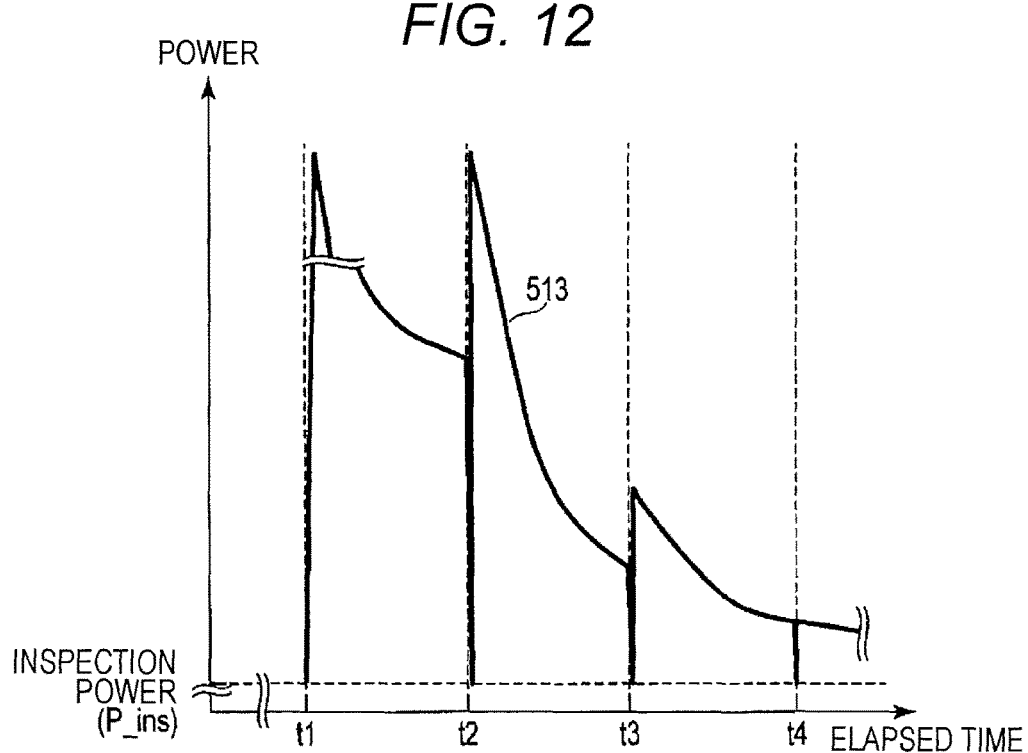
FIG. 12 is an enlarged diagram illustrating an exemplary relationship between an elapsed time and power supplied to the heat generation chip according to the first exemplary embodiment.

An enlarged diagram around the elapsed times t1 to t4 in FIG. 9 is illustrated in FIG. 11, and an enlarged diagram around the elapsed times t1 to t4 in FIG. 10 is illustrated in FIG. 12. In FIG. 11, solid line 511 indicates a change in temperature T_heat of the heat generation chip 140, and dashed-dotted line 512 indicates a change in temperature T_hfe of the first high frequency electrode 110. In FIG. 12, solid line 513 indicates power supplied to the heat generation chip 140.

As illustrated in FIG. 10, when the heat generation chip 140 starts being supplied with power, the supplied power is set at maximum power P_max. At this time, as illustrated in FIG. 9, the temperature T_heat of the heat generation chip 140 indicated in the solid line 501 increases. The temperature T_hfe of the first high frequency electrode 110 indicated in dashed-dotted line 502 also increases. Since the substrate 141 is present between the first high frequency electrode 110 and the resistance pattern 143 of the heat generation chip 140, the temperature T_hfe of the first high frequency electrode 110 is lower than the temperature T_heat of the heat generation chip 140.

The temperature T_heat of the heat generation chip 140 eventually reaches the target temperature T_target. A time until the temperature T_heat of the heat generation chip 140 reaches the target temperature T_target after the start of supplying the heat generation chip 140 with power is the period t_i. A time when the temperature T_heat of the heat generation chip 140 reaches the target temperature T_target is assumed as elapsed time t1. An interval of the elapsed times t0, t1, t2, t3 and t4 illustrated in FIGS. 9 to 12 is the period t_i.

As illustrated in FIG. 10, when the temperature T_heat of the heat generation chip 140 reaches the target temperature T_target, the supplied power is changed to the inspection power P_ins. At this time, as illustrated in FIG. 9, the temperature T_heat of the heat generation chip 140 lowers. The inspection power P_ins is so low that the temperature T_heat of the heat generation chip 140 is equal to the temperature T_hfe of the first high frequency electrode 110. The target temperature Tn_target of the heat generation chip 140 is determined as described above based on the temperature T_heat of the heat generation chip 140 at this time, or the inspection temperature T_ins which is the temperature T_hfe of the first high frequency electrode 110.

Subsequently, the supplied power is subjected to feedback control such that the temperature T_heat of the heat generation chip 140 reaches the target temperature Tn_target. Thus, as illustrated in FIG. 10, the power supplied to the heat generation chip 140 increases. At this time, as illustrated in FIG. 9, the temperature T_heat of the heat generation chip 140 increases and the temperature T_hfe of the first high frequency electrode 110 also accordingly increases. As illustrated in FIG. 10, the power supplied to the heat generation chip 140 lowers along with the increase in the temperature T_heat of the heat generation chip 140.

As illustrated in FIG. 10 and FIG. 12, the supplied power is changed to the inspection power P_ins at elapsed time t2 when the period t_i elapses after elapsed time t1. At this time, the temperature T_heat of the heat generation chip 140 is equal to the temperature T_hfe of the first high frequency electrode 110. The target temperature Tn_target of the heat generation chip 140 is reset based on the inspection temperature T_ins at this time. At this time, since the inspection temperature T_ins is close to the target temperature T_target, the target temperature Tn_target of the heat generation chip 140 is set to be close to the target temperature T_target. The supplied power is subjected to feedback control such that the temperature T_heat of the heat generation chip 140 reaches the target temperature Tn_target, and thus the temperature T_hfe of the first high frequency electrode 110 lowers as illustrated in FIG. 9 and FIG. 11.

At elapsed time t3 when the period t_i elapses from elapsed time t2, the supplied power is changed to the inspection power P_ins as illustrated in FIG. 10 and FIG. 12. At this time, the temperature T_heat of the heat generation chip 140 is equal to the temperature T_hfe of the first high frequency electrode 110. The target temperature Tn_target of the heat generation chip 140 is reset based on the inspection temperature T_ins at this time. At this time, the inspection temperature T_ins is lower than the target temperature T_target, and thus a value higher than the target temperature T_target by a difference between the inspection temperature T_ins and the target temperature T_target is set for the target temperature Tn_target of the heat generation chip 140. The supplied power is subjected to feedback control such that the temperature T_heat of the heat generation chip 140 reaches the target temperature Tn_target, and thus the temperature T_hfe of the first high frequency electrode 110 increases as illustrated in FIG. 9 and FIG. 11. Subsequently, as illustrated in FIG. 9, the temperature T_hfe of the first high frequency electrode 110 is kept around the target temperature T_target.

The temperature control of the first high frequency electrode 110 has been described herein, and a temperature of the second high frequency electrode 210 can be similarly controlled as described above.

With the temperature control according to the present exemplary embodiment, since the substrate 141 is present between the first high frequency electrode 110 and the resistance pattern 143 of the heat generation chip 140, the temperature T_hfe of the first high frequency electrode 110 can be kept around the target temperature T_target by the feedback control based on the temperature T_heat of the heat generation chip 140 irrespective of divergence between the temperature T_hfe of the first high frequency electrode 110 and the temperature T_heat of the heat generation chip 140. Further, the target temperature Tn_target of the heat generation chip 140 is updated per period t_i longer than the sampling rate of the feedback control performed in step S110, and thus the supplied power control is less likely to oscillate. Therefore, with the temperature control according to the present exemplary embodiment, the temperature T_hfe of the first high frequency electrode 110 can be kept at the target temperature T_target stably and accurately.

The interval for updating the target temperature Tn_target of the heat generation chip 140 according to the present exemplary embodiment is assumed as the period t_i until the temperature T_heat of the heat generation chip 140 reaches the target temperature T_target after the start of power supply. This is because the period t_i uses a value reflecting a thermal load imposed on the first high frequency electrode 110 or a property of a body tissue contacting with the first high frequency electrode 110. The period t_i is determined depending on a thermal load imposed on the first high frequency electrode 110, and thus the interval for updating the target temperature Tn_target of the heat generation chip 140 can be appropriately set. The interval for updating the target temperature Tn_target is not limited to the period t_i.

The update interval may be a product of t_i and a predetermined coefficient, a preset interval, or a user-set interval.

The target temperature Tn_target of the heat generation chip 140 is calculated in Equation (1) according to the present exemplary embodiment, but is not limited thereto. It may be determined as in Equation (2), for example.

$$Tn\_target = T\_target + \alpha(T\_target - T\_ins) \quad (2)$$

where α is a predetermined coefficient.

Further, according to the present exemplary embodiment, a difference between the target temperature T_target and the inspection temperature T_ins is assumed as an offset value, and the target temperature T_target added with the offset value is assumed as the target temperature Tn_target of the heat generation chip 140. The same function is possible as in the following way. That is, the target temperature Tn_target of the heat generation chip 140 is kept constant at the target temperature T_target. On the other hand, a corrected temperature Tn_heat, which is obtained assuming a difference between the target temperature T_target and the inspection temperature T_ins as an offset value, is used as the temperature T_heat of the heat generation chip 140. That is, the corrected temperature Tn_heat is given in Equation (3).

$$Tn\_heat = T\_heat - (T\_target - T\_ins) \quad (3)$$

where the inspection temperature T_ins is updated per period t_i. Even when the feedback control is performed to assume the corrected temperature Tn_heat as the target temperature T_target, the same functions as the above exemplary embodiment are obtained.

In this way, for example, the first high frequency electrode 110 and the second high frequency electrode 210 function as a heat transfer part for contacting with a body tissue and transferring heat to the body tissue. For example, the heat generation chip 140 and the heat generation chip 240, each of which is formed with an electric resistance pattern on the first surface of the substrate and is joined with the heat transfer part on the second surface of the substrate, function as a heat generation member for heating the heat transfer part when the electric resistance pattern is supplied with power. For example, the temperature acquisition circuit 373 functions as a first temperature acquisition part for acquiring a temperature of the electric resistance pattern as a first temperature and a second temperature acquisition part for acquiring a temperature of the heat transfer part as a second temperature. For example, the controller 371 functions as control part for calculating an offset value for correcting a temperature difference between a temperature of the heat transfer part and a temperature of the electric resistance pattern based on a temperature difference between the first target temperature and the second temperature per first cycle, and determining power to be supplied to the electric resistance pattern by feedback control using the first temperature having a second cycle shorter than the first cycle such that the temperature of the heat transfer part added with the offset value reaches the first target temperature. For example, the heat generation chip drive circuit 372 functions as a power supply part for supplying the electric resistance pattern with power under control of the control part.

According to the present exemplary embodiment, the temperature acquisition circuit 373 acquires a temperature of the resistance pattern 143 based on a resistance value of the resistance pattern 143 of the heat generation chip 140. Though not limited thereto, a temperature detection part such as thermocouple may be provided near the resistance pattern 143, and the temperature acquisition circuit 373 may acquire a temperature of the resistance pattern 143 by use of the temperature detection part. Further, according to the present exemplary embodiment, the power supplied to the resistance pattern 143 is switched to the inspection power P_ins per cycle T_i so that the temperature acquisition circuit 373 acquires a temperature of the resistance pattern 143 as a temperature of the first high frequency electrode 110. The temperature acquisition circuit 373 has only to acquire a temperature of the first high frequency electrode 110 per cycle T_i, and thus a temperature detection part such as thermocouple may be additionally provided on the first high frequency electrode 110, and the temperature acquisition circuit 373 may acquire a temperature of the first high frequency electrode 110 by use of the temperature detection part. The treatment apparatus 300 can function as in the present exemplary embodiment, and can obtain the same advantages even in the above way. There is configured such that various temperatures are acquired based on a resistance value of the resistance pattern 143 as in the present exemplar embodiment, and thus the energy treatment tool is downsized and simplified, and the structure of the present exemplary embodiment is preferable.

Second Exemplary Embodiment

A second exemplary embodiment according to the present invention will be described. The differences from the first exemplary embodiment will be described herein, and the same parts are denoted with the same reference numerals and the description thereof will be omitted. Also, the temperature control of the first high frequency electrode 110 is the same as the temperature control of the second high frequency electrode 210, and thus the temperature control of the first high frequency electrode 110 will be described by way of example.

According to the first exemplary embodiment, after the temperature of the heat generation chip 140 reaches the target temperature T_target, the feedback control for changing the supplied power to the inspection power P_ins and updating the target temperature Tn_target of the heat generation chip 140 per predetermined cycle is subsequently performed. To the contrary, according to the present exemplary embodiment, after the temperature T_hfe of the first high frequency electrode 110 reaches the target temperature T_target, the feedback control for changing the supplied power to the inspection power P_ins and updating the target temperature Tn_target of the heat generation chip 140 per predetermined cycle is subsequently performed. According to the present exemplary embodiment, the temperature control until the temperature T_hfe of the first high frequency electrode 110 reaches the target temperature T_target is different from that in the first exemplary embodiment. The temperature control processing according to the present exemplary embodiment will be described with reference to the flowchart illustrated in FIG. 13.

In step S201, the controller 371 starts counting the first elapsed time t_c1 indicating an elapsed time after the heat generation chip 140 starts heating the first high frequency electrode 110. In step S202, the controller 371 causes the heat generation chip drive circuit 372 to supply the heat generation chip 140 with maximum power Pmax. In step S203, the controller 371 acquires the temperature T_heat of the heat generation chip 140 from the temperature acquisition circuit 373.

In step S204, the controller 371 calculates the temperature T_hfe of the first high frequency electrode 110 based on the temperature T_heat of the heat generation chip 140. Herein, Equation (4) may be employed for calculating the temperature T_hfe of the first high frequency electrode 110, for example.

$$T\_hfe = T\_heat - C1 \times P \quad (4)$$

where C1 denotes a predetermined correction coefficient, and P denotes power currently supplied to the heat generation chip 140. Equation (4) is based on the fact that a temperature difference between the temperature T_heat of the heat generation chip 140 and the temperature T_hfe of the first high frequency electrode 110 is proportional to the supplied power P. The correction coefficient C1 is previously determined because it depends on the property of the heat generation chip 140.

In step S205, the controller 371 determines whether the temperature T_hfe of the first high frequency electrode 110 is higher than the target temperature T_target. When it is determined that the temperature T_hfe of the first high frequency electrode 110 is not higher than the target temperature T_target, the processing proceeds to step S206. In step S206, the controller 371 determines the power P to be supplied to the heat generation chip 140 based on the temperature T_hfe of the first high frequency electrode 110 such that the temperature T_hfe of the first high frequency electrode 110 reaches the target temperature T_target. Herein, the power P is determined by use of PD control or PID control. In step S207, the controller 371 instructs the heat generation chip drive circuit 372 to supply the heat generation chip 140 with the power P. Thereafter, the processing returns to step S203. That is, until the temperature T_hfe of the first high frequency electrode 110 reaches the target temperature T_target, the temperature T_hfe of the first high frequency electrode 110 is calculated and the feedback control is performed based on the value.

In step S205, when it is determined that the temperature T_hfe of the first high frequency electrode 110 is higher than the target temperature T_target, the processing proceeds to step S208. The processings in step S208 to step S216 are the same as the processings in step S105 to step S113 according to the first exemplary embodiment. In the present exemplary embodiment, the period t_i is set at any value.

The processings in step S208 to step S216 are the same as in the first exemplary embodiment, and thus the description thereof will be omitted and simply denoted, that is, the controller 371 stops supplying power in step S208, supplies the heat generation chip 140 with the inspection power P_ins in step S209, acquires the inspection temperature T_ins of the heat generation chip 140 in step S210, and calculates the target temperature Tn_target of the heat generation chip 140 by use of the inspection temperature T_ins in step S211. The controller 371 resets the second elapsed time t_c2 in step S212, and performs the target temperature control operation in step S213. The controller 371 determines whether the first elapsed time is shorter than the heating time in step S214, and if not shorter, proceeds to step S216 to stop supplying power and to terminate the processing. On the other hand, when the first elapsed time is shorter than the heating time, the controller 371 determines whether the second elapsed time is shorter than the period t_i in step S215, and if shorter, the processing returns to step S213, otherwise, the processing returns to step S208.

As described above, according to the present exemplary embodiment, the temperature control method is changed before and after the temperature T_hfe of the first high frequency electrode 110 reaches the target temperature T_target. That is, before the temperature T_hfe of the first high frequency electrode 110 reaches the target temperature T_target, the temperature T_hfe of the first high frequency electrode 110 is calculated based on Equation (4), and the feedback control is performed based on the value. On the other hand, after the temperature T_hfe of the first high frequency electrode 110 reaches the target temperature T_target, as in the first exemplary embodiment, the target temperature Tn_target of the heat generation chip 140 is set per period t_i, and the feedback control is performed such that the temperature T_heat of the heat generation chip 140 reaches the target temperature Tn_target. Herein, the control until the temperature T_hfe of the first high frequency electrode 110 reaches the target temperature T_target will be called first control, and the control after the temperature T_hfe of the first high frequency electrode 110 reaches the target temperature T_target will be called second control.

Figure 14:
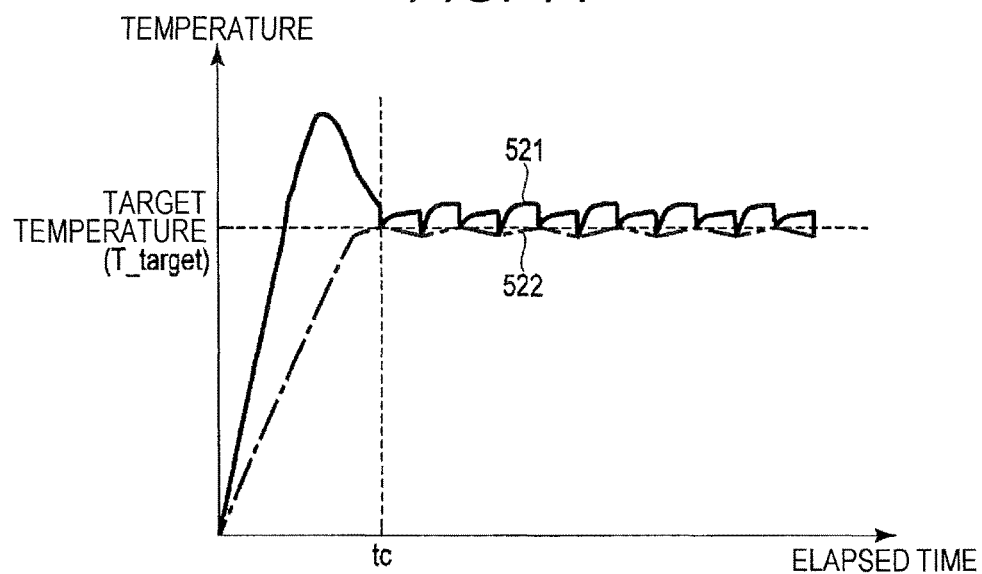
FIG. 14 is a diagram illustrating an exemplary relationship between an elapsed time, and the heat generation chip and the first high frequency electrode according to the second exemplary embodiment.
Figure 15:
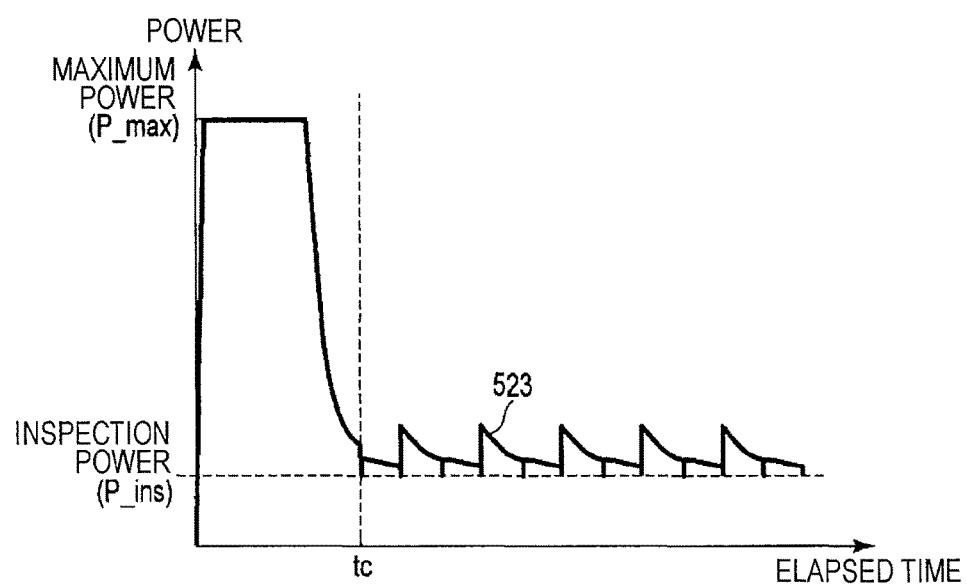
FIG. 15 is a diagram illustrating an exemplary relationship between an elapsed time and power supplied to the heat generation chip according to the second exemplary embodiment.

A change in temperature of the heat generation chip 140 and a change in temperature of the first high frequency electrode 110 relative to an elapsed time during the above processings are illustrated in FIG. 14. In FIG. 14, solid line 521 indicates a change in temperature T_heat of the heat generation chip 140, and dashed-dotted line 522 indicates a change in temperature T_hfe of the first high frequency electrode 110. Further, a change in power to be supplied to the heat generation chip 140 relative to an elapsed time illustrated in FIG. 14 is illustrated in FIG. 15. In FIG. 15, solid line 523 indicates power to be supplied to the heat generation chip 140. The elapsed time tc indicates an elapsed time when the first control is switched to the second control.

In the second control, the temperature control is stable, but the time until the temperature of the first high frequency electrode reaches the target temperature T_target is longer than that in the first control because the inspection power P_ins is periodically supplied. On the other hand, in the first control, the time until the temperature of the first high frequency electrode 110 reaches the target temperature T_target is shorter than that in the second control, but the supplied power easily oscillates in the first control when the temperature T_hfe of the first high frequency electrode 110 is close to the target temperature T_target. In the present exemplary embodiment, while the temperature T_hfe of the first high frequency electrode 110 is away from the target temperature T_target, or while the temperature T_hfe of the first high frequency electrode 110 is reaching the target temperature T_target, the first control with a rapid increase in temperature is employed. On the other hand, when the temperature T_hfe of the first high frequency electrode 110 is close to the target temperature T_target, or after the temperature T_hfe of the first high frequency electrode 110 reaches the target temperature T_target, the highly stable second control is employed. Therefore, according to the present exemplary embodiment, the advantages of the first control and the second control may be employed, respectively.

Figure 8:
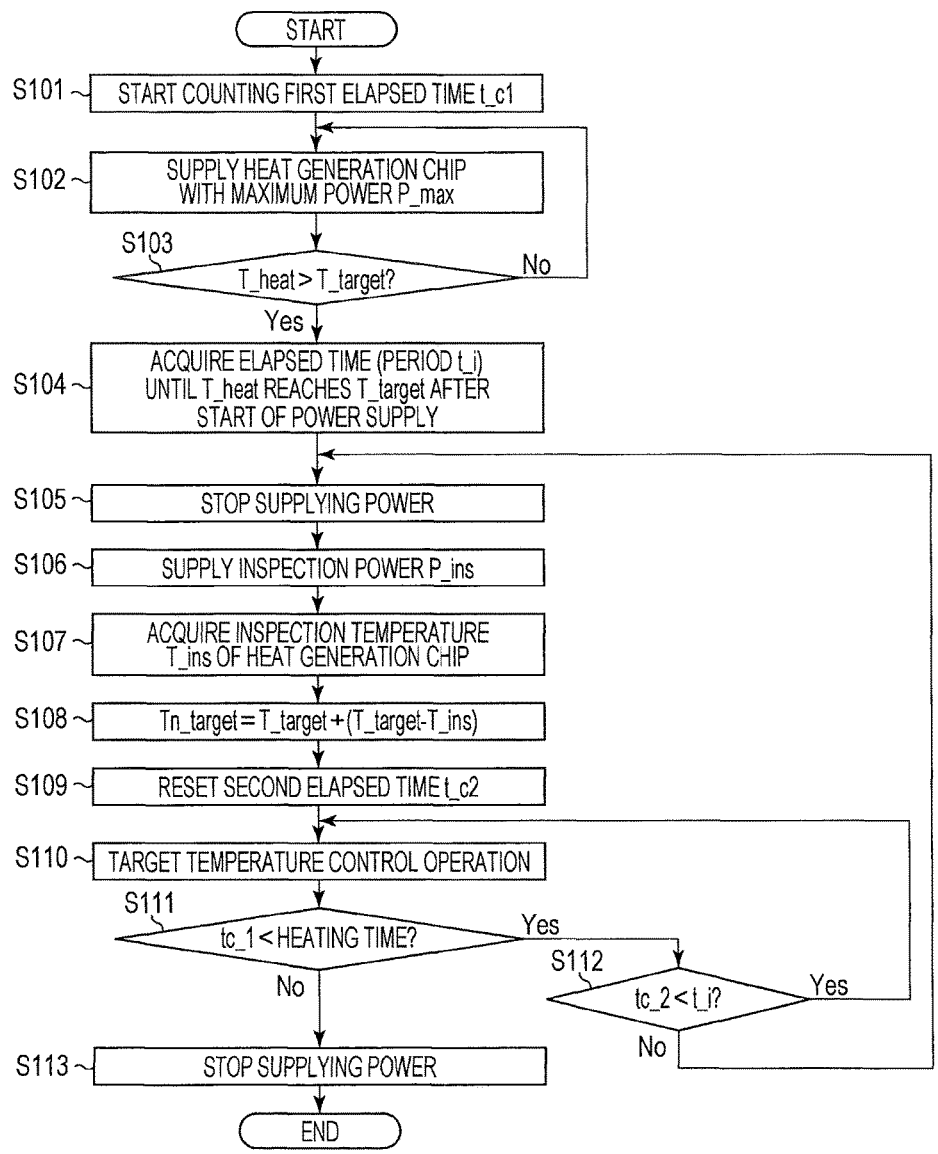
FIG. 8 is a flowchart illustrating an exemplary power control processing according to a first exemplary embodiment.
Figure 13:
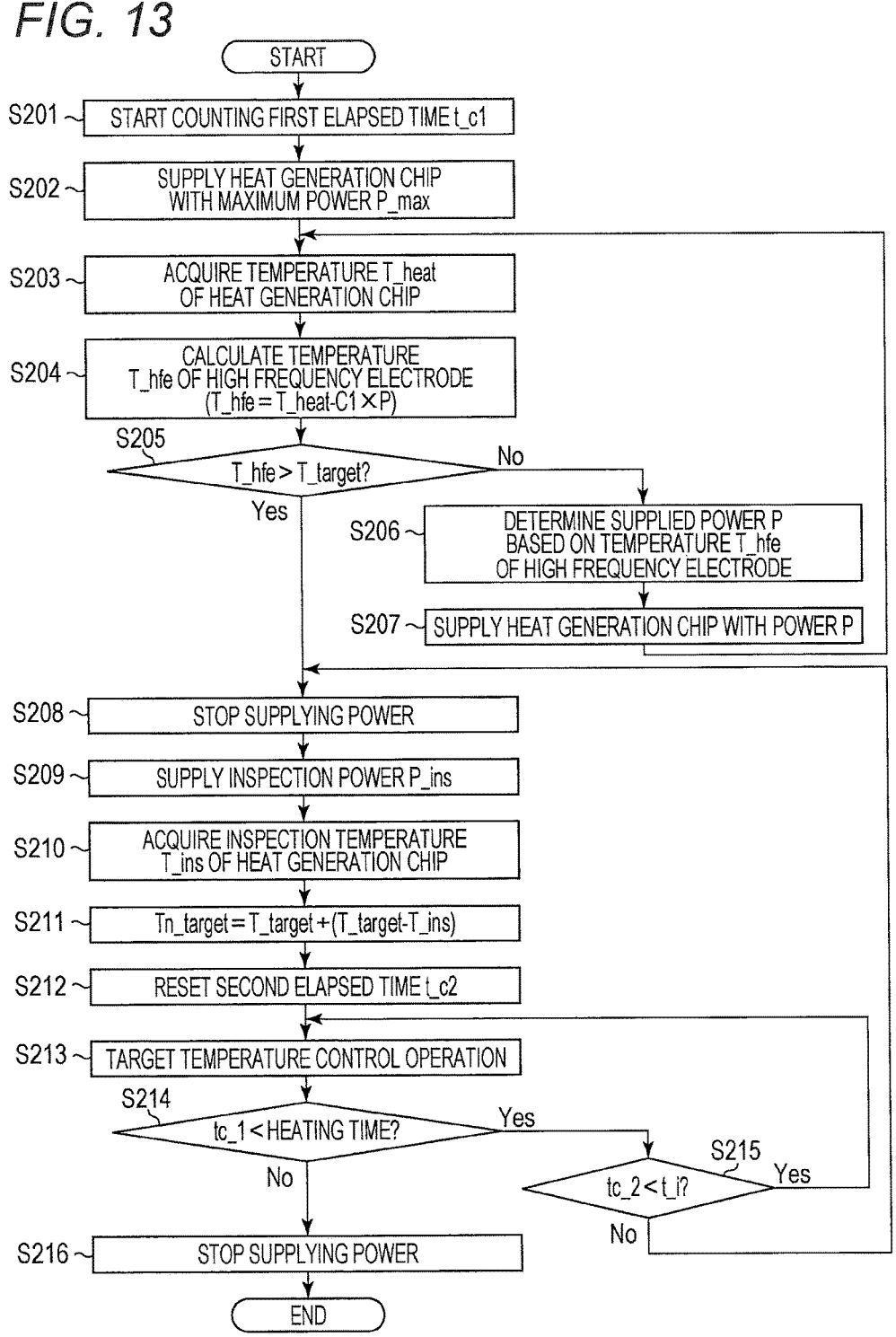
FIG. 13 is a flowchart illustrating an exemplary power control processing according to a second exemplary embodiment.

The processings and their order described with reference to FIG. 8 or FIG. 13 are not limited to the above description, and the processings may be increased or decreased or the order of processings may be changed as needed, such as rearranged, within the scope. The energy treatment tool 310 is configured to be supplied with high frequency energy and thermal energy, but may have other functions if it is configured to be supplied with thermal energy, even if supplied with high frequency energy. The energy treatment tool 310 may take various forms. For example, it may be pressed against a body tissue, not limited to gripping a body tissue.

The invention claimed is:

1. A treatment apparatus for treating a body tissue, the treatment apparatus comprising:
 a drive circuit configured to be controlled to supply power;
 an electric resistance pattern configured to generate heat based on the power supplied by the drive circuit;
 a heat transfer plate configured to contact the body tissue, wherein the heat transfer plate is arranged to be in thermal communication with the electric resistance pattern to transfer the heat generated by the electric resistance pattern to the body tissue;
 a temperature acquisition circuit configured to be controlled to acquire a temperature of the electric resistance pattern; and
 a controller configured to:
  in a first cycle,
   control the drive circuit to supply a first power to the electric resistance pattern;
   control the temperature acquisition circuit to acquire a first temperature of the electric resistance pattern; and
   control the drive circuit to stop supplying the first power when the first temperature of the electric resistance pattern reaches a target temperature of the heat transfer plate;
  in a subsequent cycle after the first cycle,
   control the drive circuit to supply an inspection power to the electric resistance pattern after stopping supplying the first power, wherein the inspection power is lower than the first power;
   control the temperature acquisition circuit to acquire a second temperature of the electric resistance pattern after elapse of a predetermined time from start of supply of the inspection power to the electric resistance pattern;
   calculate an offset value based on a difference between the target temperature of the heat transfer plate and the second temperature of the electric resistance pattern;
   calculate a subsequent target temperature based on the offset value; and
   calculate a second power to be supplied to the electric resistance pattern to heat the electric resistance pattern to the subsequent target temperature, wherein the second power is lower than the first power and is higher than the inspection power; and
   control the drive circuit to supply the second power to the electric resistance pattern.

2. The treatment apparatus according to claim 1, wherein the temperature acquisition circuit is configured to acquire the temperature of the electric resistance pattern based on a resistance value of the electric resistance pattern.

3. The treatment apparatus according to claim 1, wherein the offset value is calculated by a relationship of:

$T\_offset = T\_target - T\_ins,$ where $T\_offset$ is the offset value, $T\_target$ is the target temperature of the heat transfer plate, and $T_{ins}$ is the second temperature of the electric resistance pattern, and
wherein the subsequent target temperature is calculated by a relationship of:

$Tn\_target = T\_target + T\_offset,$ where $Tn\_target$ is the subsequent target temperature.

4. The treatment apparatus according to claim 1, wherein the controller is configured to repeat the subsequent cycle a plurality of times in a feedback loop to control a temperature of the heat transfer plate to approach the target temperature of the heat transfer plate.

5. A method for controlling a treatment apparatus to treat a body tissue,
 wherein the treatment apparatus comprises:
  a drive circuit configured to be controlled to supply power;
  an electric resistance pattern configured to generate heat based on the power supplied by the drive circuit;
  a heat transfer plate configured to contact the body tissue, wherein the heat transfer plate is arranged to be in thermal communication with the electric resistance pattern to transfer the heat generated by the electric resistance pattern to the body tissue; and
  a temperature acquisition circuit configured to be controlled to acquire a temperature of the electric resistance pattern;
 wherein the method comprises:
  in a first cycle,
   controlling the drive circuit to supply a first power to the electric resistance pattern;
   controlling the temperature acquisition circuit to acquire a first temperature of the electric resistance pattern; and
   controlling the drive circuit to stop supplying the first power when the first temperature of the electric resistance pattern reaches a target temperature of the heat transfer plate; and
  in a subsequent cycle after the first cycle,
   controlling the drive circuit to supply an inspection power to the electric resistance pattern after stopping supplying the first power, wherein the inspection power is lower than the first power;
   controlling the temperature acquisition circuit to acquire a second temperature of the electric resistance pattern after elapse of a predetermined time from start of supply of the inspection power to the electric resistance pattern;
   calculating an offset value based on a difference between the target temperature of the heat transfer plate and the second temperature of the electric resistance pattern;
   calculating a subsequent target temperature based on the offset value;
   calculating a second power to be supplied to the electric resistance pattern to heat the electric resistance pattern to the subsequent target temperature, wherein the second power is lower than the first power and is higher than the inspection power; and
   controlling the drive circuit to supply the second power to the electric resistance pattern.

6. A treatment apparatus for treating a body tissue, the treatment apparatus comprising:
 a drive circuit configured to be controlled to supply power;
 an electric resistance pattern configured to generate heat based on the power supplied by the drive circuit;
 a heat transfer plate configured to contact the body tissue, wherein the heat transfer plate is arranged to be in thermal communication with the electric resistance pattern to transfer the heat generated by the electric resistance pattern to the body tissue;

a temperature acquisition circuit configured to be controlled to acquire a temperature of the electric resistance pattern; and a controller configured to:
  in a first cycle,
    control the drive circuit to supply a first power to the electric resistance pattern;
    control the temperature acquisition circuit to acquire a first temperature of the electric resistance pattern; and
    control the drive circuit to stop supplying the first power when the first temperature of the electric resistance pattern reaches a target temperature of the heat transfer plate;
  in a subsequent cycle after stopping supplying the first power when the first temperature of the electric resistance pattern reaches the target temperature of the heat transfer plate in the first cycle,
    control the temperature acquisition circuit to acquire a second temperature of the electric resistance pattern;
    calculate an offset value based on a difference between the target temperature of the heat transfer plate and the second temperature of the electric resistance pattern;
    calculate a subsequent target temperature based on the offset value; and
    calculate a second power to be supplied to the electric resistance pattern to heat the electric resistance pattern to the subsequent target temperature; and
    control the drive circuit to supply the second power to the electric resistance pattern.

* * * * *